United States Patent [19]

Hallworth et al.

[11] 4,353,365

[45] * Oct. 12, 1982

[54] DEVICE FOR DISPENSING MEDICAMENTS

[75] Inventors: Gerald W. Hallworth, Ware; David Clough, Bishop Stortford, both of England

[73] Assignee: Glaxo Group Limited, London, England

[*] Notice: The portion of the term of this patent subsequent to Jun. 10, 1997, has been disclaimed.

[21] Appl. No.: 213,309

[22] Filed: Dec. 5, 1980

[30] Foreign Application Priority Data

Dec. 6, 1979 [GB] United Kingdom ............... 7942208

[51] Int. Cl.³ .......................................... A61M 15/00
[52] U.S. Cl. ................................ 128/203.15; 222/87; 222/83.5
[58] Field of Search ................... 128/203.15; 222/630, 222/81, 88, 87, 83, 83.5

[56] References Cited

U.S. PATENT DOCUMENTS 4,206,758 6/1980 Hallworth et al. ............ 128/203.15

Primary Examiner—Henry J. Recla

Attorney, Agent, or Firm—McAulay, Fields, Fisher, Goldstein & Nissen

[57] ABSTRACT

A device by which powdered medicaments can be orally or nasally administered to a patient comprises a body shell defining a portion of a chamber. A nozzle or mouthpiece is located at the forward end of the body shell. The body shell is open at the rear end. A sleeve is fitted on the outside of the rear end portion of the body shell and is rotatable and axially movable with respect to it. The sleeve has a rear wall which closes the open rear end of the chamber. A capsule retaining means extends through the rear wall of the sleeve into the chamber. The capsule retaining means has an external entry opening for a capsule at the rear of the sleeve. An abutment is fixed inside the chamber in such a position with respect to the retaining means that a capsule retained in the retaining means and projecting from it into the chamber will engage the abutment when the sleeve is rotated with respect to the body shell. This separates the projecting portion of the capsule from the remainder of the capsule. A grid or guard prevents the separated portion of the capsule from passing through the nozzle or mouthpiece. An air inlet opening extends through the rear wall of the sleeve into the chamber.

5 Claims, 5 Drawing Figures

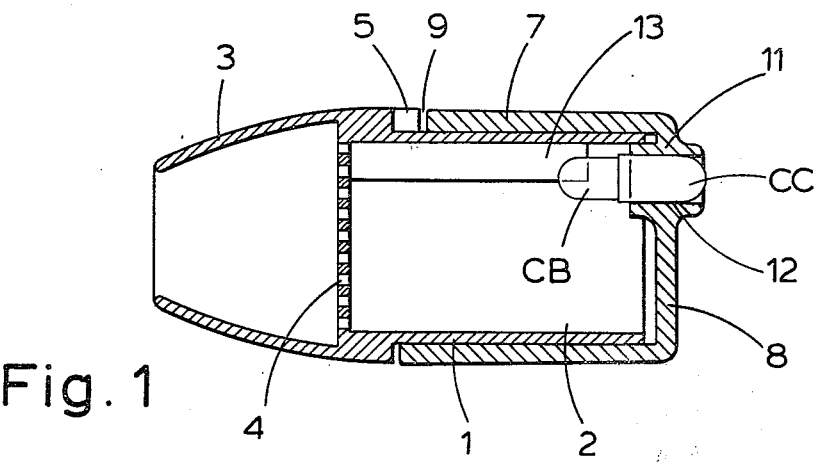
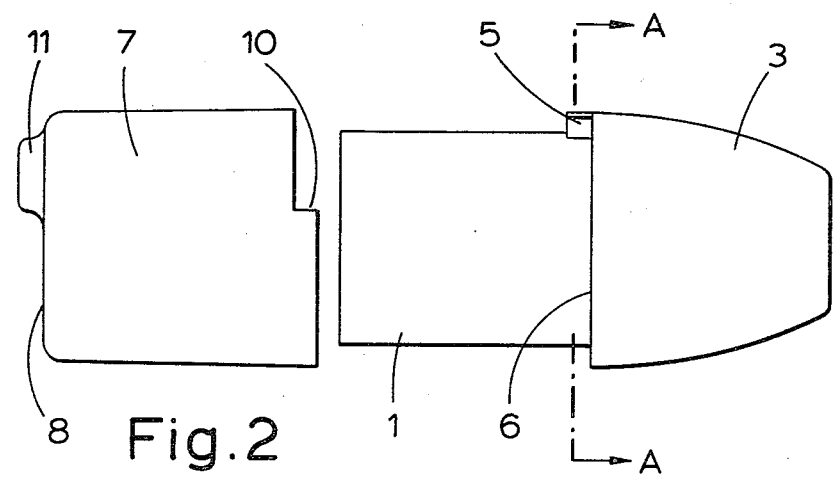
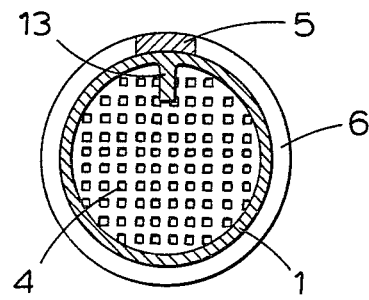
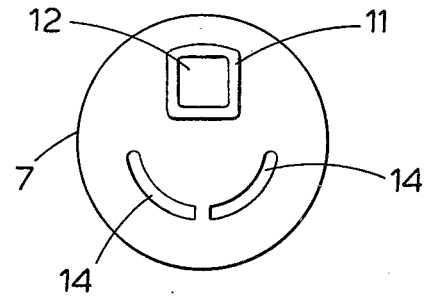

DEVICE FOR DISPENSING MEDICAMENTS

BACKGROUND OF THE INVENTION

It is well known to administer powdered medicaments to the lung bronchioles of a patient by means of inhalation devices having mouthpieces which enable the medicament to be inhaled through the mouth of the patient. The "mouthpiece" may if desired, be modified so that it is possible to inhale through a nostril of the patient. The medicament in such cases is supplied in gelatine capsules which are inserted in the device and opened in some suitable way after which inhalation through the mouthpiece will cause the powdered medicament to be released from the capsule and pass into the patient.

Capsules containing such medicaments are generally of gelatine and of elongated "torpedo" shape and are constructed in two parts, one of which (called the capsule body) is partly enclosed within the other (called the capsule cap). The contacting portions of the two capsule parts are often provided with grooves and/or ribs which have the effect of "locking" the two capsule parts together. The inhalation devices for use with such capsules normally have a chamber arranged to receive a capsule containing the medicament. An air inlet aperture or a plurality of such apertures, lead into the chamber in a generally transversal direction and air from the chamber can be inhaled through a nozzle. The air inlet aperture or apertures is/are so arranged that the air flow caused by inhalation through the nozzle will cause the contents of an opened capsule within the chamber to be released and withdrawn through the nozzle.

BRIEF SUMMARY OF THE PRESENT INVENTION

According to the present invention, there is provided a device comprising a body shell defining a portion of a chamber which has a nozzle at a forward end and which is open at the rear end, a sleeve fitted on the outside of the body shell and rotatable with respect to it and having a rear wall closing the open rear end of the chamber, a capsule retaining means extending through the said rear wall of the sleeve into the chamber and having an external entry opening for a capsule at the rear of the sleeve, an abutment fixed inside the chamber in such a position with respect to the capsule retaining means that a capsule retained in the retaining means and projecting from it into the chamber will engage the abutment when the sleeve is rotated with respect to the body shell thereby to separate the projecting portion of the capsule from the remainder of the capsule, a guard for preventing the separated portion of the capsule from passing through the nozzle and an air inlet opening extending through the said rear wall of the sleeve into the chamber. A stop may be provided to limit the rotation of the sleeve with respect to the body shell.

BRIEF DESCRIPTION OF THE ACCOMPANYING SCHEMATIC DRAWINGS

FIG. 1 is a sectional elevation of a device according to the invention,

FIG. 2 is an exploded elevation,

FIG. 3 is a rear view of the device,

FIG. 4 is a section on the line A—A of FIG. 2,

DESCRIPTION OF A PREFERRED EMBODIMENT

Figure 5:
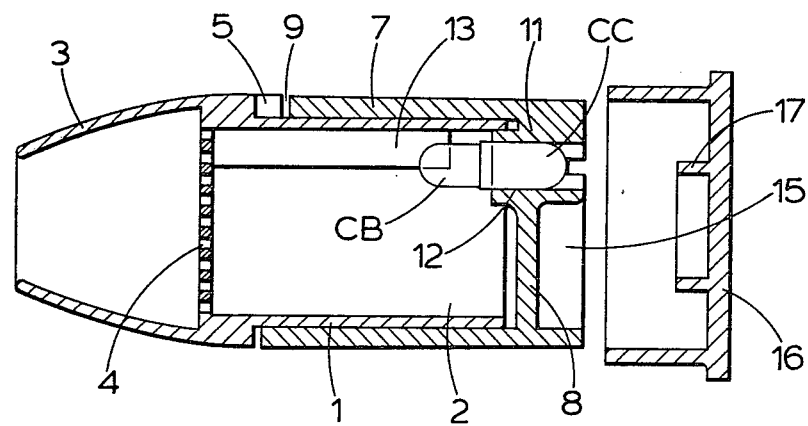
FIG. 5 is a view similar to FIG. 1 illustrating a modification.

In the illustrated embodiment of the invention, an inhalation device is conveniently, but not essentially of a plastics material. The device comprises a cylindrical body shell 1, the interior of which defines a portion of a cylindrical capsule-receiving chamber 2. Secured to one end of the body shell, herein considered to be the forward end, is a nozzle or mouthpiece 3. A perforated guard 4, which defines the front end of the chamber 2, is fixed inside the body shell 1 and prevents portions of a capsule inside the chamber 2 being withdrawn through the mouthpiece 3 when a patient inhales. An abutment 5 serving as a stop for a purpose hereinafter to be described, is located on the outside of the body shell 1. This stop or abutment 5 projects to the rear of a shoulder 6 extending around the body shell 1 at the rear of the mouthpiece 3. The rear end of the body shell 1 is open.

A cylindrical sleeve 7 is fitted on the rear end portion of the body shell 1. The sleeve is both rotatable and axially slidable on the body shell 1. The sleeve has a rear end wall 8 which closes the open rear end of the body shell 1 and thus of the chamber 2. The sleeve 7 has a recessed forward end, the recess being formed by a part cylindrical extension of the sleeve. The sleeve 7 may be slid off the rear end portion of the body shell 1 to provide access to the interior of the chamber 2, but when the device is in use by a patient, the forward or recessed end of the sleeve abuts against the shoulder 6 at the rear end of the mouthpiece thereby to define a slot 9 in which the stop 5 is located. The ends of the recess in the forward end of the sleeve form abutments 10 against which the stop 5 can engage when the sleeve 7 is rotated in one direction or other with respect to the body shell so that rotation of the sleeve 7 is limited.

A capsule retaining means 11 in the form of a tube is arranged at, and extends through, the rear end wall 8 of the sleeve 7. A forward end portion of the retaining means 11 extends into the rear end of the sleeve 7, i.e. into the chamber 2, as clearly shown in FIG. 1 of the drawings. The retaining means 11 has a passage 12 which opens at the forward end into the chamber 2 and at the rear end opens externally of the rear wall 8 of the sleeve. A capsule may be entered through the open rear end of this passage and retained in the passage. The retaining means 11 is of such a length that when the sleeve 7 is in its fully forward position on the body shell 1 and a capsule is pushed, preferably body first, into the passage 12, the capsule cap (CC) will be retained in the retaining means and the capsule body (CB) will protrude into the chamber as illustrated in FIG. 1. The retaining means 11 may be a separate member fitted into the rear wall 8 of the sleeve 7 or it may be, as illustrated, an integral part of the sleeve 7, i.e. the tube 11 and the sleeve 7 may be a single moulding. As shown in FIG. 3, the passage 12 in the retaining means 11 is substantially square in cross-section. The size and shape of the passage 12 is such that the retaining means 12 will squeeze and deform at least part of the overlapping portions of the capsule body (CB) and the capsule cap (CC), thereby to break or weaken the lock between the two capsule parts.

An abutment in the form of a fin or rib 13 is fixed to the inside of the body shell 1. The abutment 13 and the retaining means 11 are so disposed with respect to each other that when the body (CB) of a capsule which has been inserted into the passage 12 of the retaining means projects from the retaining means into the chamber 2, the projecting body (CB) of the capsule will engage a side of the fin or rib 13 when the sleeve 7 is rotated with respect to the body shell thereby to separate the two capsule parts. The forward separated capsule portion will, of course, fall into the chamber 2 and the remainder of the capsule will of course be retained in the passage 12 of the capsule retaining means.

Below the retaining means 11, is an air inlet formed by two arcuate slots 14 extending through the rear wall 8 of the sleeve and opening into the chamber 2. Alternatively, the slots 14 may be replaced by a single linear or arcuate slot or by a row of holes or by a single round hole or a group of holes not arranged in rows. When air is aspirated by a patient through the nozzle or mouthpiece 3, the capsule portion (CB) separated from the remainder of the capsule and disposed in the chamber 2 will be agitated. This agitation serves to empty powder from the separated capsule body (CB). The abutment 13 will assist in this because it acts as a "kick-bar" in that the capsule body repeatedly collides with the rib. The agitation and vibration produced by such collision assists in the operation of emptying medicament from the portion of the capsule in the chamber 2. Medicament in the portion of the capsule remaining in the retaining means will of course be withdrawn as the patient aspirates through the mouthpiece or nozzle 3.

If desired, the fin or rib 13 may be shorter than as illustrated in FIG. 1, and only of sufficient length to engage the projecting portion (CB of the capsule held in the retaining means 11 and a separate "kick-bar" or a plurality of such kick-bars may then, if desired, be provided.

In the modification illustrated in FIG. 5, the retaining means 11 opens into a compartment 15 which is a rearward extension of the sleeve 7 and which is closed by a removable cover 16. The compartment may have a suitable air inlet and/or the cover may be removed when the device is in use. The cover has pusher means in the form of an inwardly projecting ring 17 of sufficient depth to engage the cap (CC) of a capsule engaged in the entry opening of the retaining means 11 and press it forward when the cover is fitted in its closed position. To make this possible, the wall of the retaining means has lead-in portion with a suitable groove so that the ring 17 can enter the opening. When a new capsule is inserted in the retaining means, the entering capsule body (CB) will push the capsule cap (CC) of the previously used capsule or of the retaining means and into the chamber.

In a further modification, the pusher means is not a ring but is a peg or the like engageable with a capsule in the retaining means.

We claim:

1. An inhalation device by which powdered medicaments can be orally or nasally administered to a patient comprising a body shell defining a portion of a chamber which has a nozzle at a forward end and which is open at the rear end, a sleeve fitted on the outside of the body shell and rotatable with respect to it and having a rear wall closing the open rear end of the chamber, a capsule retaining means extending through the said rear wall of the sleeve into the chamber and having an external entry opening for a capsule at the rear of the sleeve, said capsule retaining means being sized to retain a capsule inserted therein with a portion of the capsule extending into said chamber, an abutment fixed inside the chamber in such a position with respect to the capsule retaining means that the capsule retained in the retaining means and projecting from it into the chamber will engage the abutment when the sleeve is rotated with respect to the body shell thereby to separate the projecting portion of the capsule from the remainder of the capsule, a guard for preventing the separated portion of the capsule from passing through the nozzle, and an air inlet opening extending through the said rear wall of the sleeve into the chamber.

2. A device as claimed in claim 1, which has a stop to limit rotation of the sleeve with respect to the body shell.

3. A device as claimed in claim 1, wherein the body shell has a rearwardly directed shoulder from which a stop extends rearwardly and the sleeve has a recessed forward end engaged with the shoulder to define a slot in which the stop is located, the stop being engaged with opposite ends of the slot when the sleeve and body shell are rotated with respect to one another thereby to limit relative rotation between the sleeve and the body shell.

4. A device as claimed in claim 3, wherein the sleeve has at the rear an extension compartment into which the entry opening of the retaining means opens, the extension compartment having a removable cover provided with pusher means which, when the cover is fitted to the extension compartment, engages the end of a capsule retained in the retaining means, and pushes the capsule forward.

5. A device as claimed in claim 4, wherein the pusher means is an annular ring inside the cover and a groove in said retaining means adjacent the entry opening thereof sized and positioned to receive said annular ring therein, whereby said ring extends into said retaining means.

* * * * *